US005804396A

United States Patent [19]
Plowman

[11] Patent Number: 5,804,396
[45] Date of Patent: Sep. 8, 1998

[54] ASSAY FOR AGENTS ACTIVE IN PROLIFERATIVE DISORDERS

[75] Inventor: Gregory D. Plowman, San Carlos, Calif.

[73] Assignee: Sugen, Inc., Redwood City, Calif.

[21] Appl. No.: 322,868

[22] Filed: Oct. 12, 1994

[51] Int. Cl.$^6$ ........................ G01N 33/574; G01N 33/53; G01N 33/567; G01N 33/48

[52] U.S. Cl. .......................... 435/7.23; 435/7.2; 436/63; 436/64

[58] Field of Search .................................. 435/7.2, 7.23; 436/63, 64

[56] References Cited

U.S. PATENT DOCUMENTS

| 4,343,940 | 8/1982 | Kreighbaum et al. ................... 544/283 |
| 4,447,608 | 5/1984 | Jones et al. ............................. 544/287 |
| 4,757,072 | 7/1988 | Kabbe et al. ............................ 514/257 |
| 5,316,553 | 5/1994 | Kaul et al. .................................. 8/639 |

FOREIGN PATENT DOCUMENTS

| 0520722 | 12/1992 | European Pat. Off. . |
| 0562734 | 9/1993 | European Pat. Off. . |
| 9220642 | 11/1992 | WIPO . |

OTHER PUBLICATIONS

Gura. T. "Systems for identifying new drugs are often faulty" Science. vol. 278. pp. 1041–1042, Nov. 7, 1997.

Dermer G. "Another Anniversary for the war on Cancer" Bio/Technology. vol. 12. p. 320, Mar. 1994.

King et al, "High throughput assay for inhibitors of the epidermal growth factor receptor–associated tyrosine kinase" Life Sciences, vol. 53, pp. 1465–1472, 1993.

Aaronson, "Growth Factors and Cancer," *Science*, 254:1146–1153 (1991).

Allen et al., "Modulation of CD4 by Suramin," *Clin. Exp. Immunol.* 91:141–156 (1993).

Anafi et al., "Tyrphostin–Induced Inhibition of p210$^{bcr-abl}$ Tyrosine Kinase Activity Induces K562 to Differentiate," *Blood* 82:3524–3529 (1993).

Andrews et al., "Report of the AVMA Panel on Euthanasia," *Journal of American Veterinary Medical Assoc.* 202:229–249 (1993).

Bacus et al., "A Ligand for the erbB–2 Oncongene Product (gp30) Induces Differentiation of Human Breast Cancer Cells," *Cell Growth and Diff.* 3:401–411 (1992).

Baker et al., "Induction of Acetylcholine Receptor Clustering By Native Polystyrene Beads: Implication of an endogenous muscle–derived signalling system," *J. Cell Sci.* 102:543–555 (1992).

Barker et al., "In vitro activity of non–glutamate containing quinazoline–based thymidylate synthase inhibitors," *Proc. of Am. Assoc. for Cancer Research* 32:327 (1991).

Bertino, "Toward Improved Selectivity in Cancer Chemotherapy: The Richard and Hinda Rosenthal Foundation Award Lecture," *Cancer Research* 39:293–304 (1979).

Bilder et al., "Tyrphostins inhibit PDGF–induced DNA synthesis and associated early events in smooth muscle cells," *Am. J. Physiol.* 260(Cell Physiol.29):C721–C730 (1991).

Brunton et al., "Anti–Tumor Activity of Novel Tyrphostins in Breast Cancer Cells," *Proceedings of Amer. Assoc. Cancer Rsch.* 33:558 (1992).

Bryckaert et al., "Inhibition of Platelet–Derived Growth Factor–Induced Mitogenesis and Tyrosine Kinase Activity in Cultured Bone Marrow Fibroblasts by Tyrphostins," *Exp. Cell Research*, 199:255–261 (1992).

Burke et al., "Bicyclic Compounds as Ring–Constrained Inhibitors of Protein Tyrosine Kinase p56$^{lck}$ $^1$," *J. Med. Chem.* 36:425–432 (1993).

Burke et al., "Arylamides of Hydroxylated Isoquinolines as Protein–Tyrosine Kinase Inhibitors," *BioOrganic Med. Chem. Letters* 2:1771–1774 (1992).

Caraglia et al., "Cytosine Arabinoside Increases the Binding of $^{125}$I–Labelled Epidermal Growth Factor and $^{125}$I–Transferrin And Enhances the In Vitro Targeting of Human Tumour Cells With Anti–(Growth Factor Receptor)mAb," *Cancer Immunol. Immunother.* 37:150–156 (1993).

Caraway and Cantley, "A Neu Acquaintance for ErbB3 and ErbB4: A Role for Receptor Hereodimerization in Growth Signaling", *Cell* 78:5–8 (1994).

Carraway et al., "The erbB3 Gene Product Is a Receptor for Heregulin", *J. Biol. Chem.* 269:14303–14306 (1994).

Chou and Haman, "Characterization of a member of the immunoglobulin gene superfamily that possibly represents an additional class of growth factor receptor," *Proc. Natl. Acad. Sci. USA* 88:4897–4901 (1991).

Curtin et al., "Inhibition of the growth of human hepatocellular carcinoma in vitro and in athymic mice by a quinazoline inhibitor of thymidylate synthase, CB3717," *Br. J. Cancer* 53:361–368 (1986).

Culouscou et al., "Characterization of a Breast Cancer Cell Differentiation Factor That Specifically Activates the HER4/p180$^{erbB4}$ Receptor", *J. Biol. Chem.* 268:18407–18410 (1993).

Dati et al., "Inhibition of c–erbB–2 oncogene expression by estrogens in human breast cancer cells", *Oncogene* 5:1001–1006 (1990).

Decker and Lohmann–Matthes, "A quick and simple method for the quantitation of lactate dehydrogenase release in measurements of cellular cytotoxicity and tumor necrosis factor (TNF) activity," *J. Immunol. Methods*, 115:61–69 (1988).

(List continued on next page.)

*Primary Examiner*—Sheela Huff
*Assistant Examiner*—Yvonne Eyler
*Attorney, Agent, or Firm*—Lyon & Lyon LLP

[57] ABSTRACT

Method for identifying an agent for treatment of a proliferative disorder, comprising the steps of assaying a potential agent for activity in inhibition of signal transduction by a HER2/HER3 or HER2/HER4 or HER3/HER4 heterodimer. Method of screening for an agent that selectively inhibits the kinase activity of a heterodimer having one catalytically inactive component.

18 Claims, No Drawings

OTHER PUBLICATIONS

Dolle et al., "5,7–Dimethoxy–3–(4–pyridinyl) quinoline Is a Potent and Selective Inhibitor of Human Vascular β–Type Platelet–Derived Growth Factor Receptor Tyrosine Kinase," *J. Med. Chem.* 37:2627–2629 (1994).

Dong et al., "Activation of Tumoricidal Properties in Macrophages by Lipopolysaccharide Requires Protein–Tyrosine Kinase Activity," *J. Leukocyte Biology* 53:53–60 (1993).

Dong et al., "Protein Tyrosine Kinase Inhibitors Decrease Induction of Nitric Oxide Synthase Activity in Lipopolyaccharide–Responsive and Lipopolysaccharide–Nonresponsive Murine Macrophages," *J. Immunol.* 151(5):2717–2724 (1993).

Fernandes et al., "Biochemical and Antitumor Effects of 5,8–Dideazaisopteroylglutamate, a Unique Quinazoline Inhibitor of Thylmidylate Synthase," *Cancer Research* 43:1117–1123 (1983).

Ferris et al., "Synthesis of Quinazoline Nucleosides from Ribose and Anthranilonitrile. Application of Phase–Transfer Catalysis in Nucleoside Synthesis," *J. Org. Chem.*, 44(2):173–178 (1979).

Fry et al., "New insights into protein–tyrosine kinase receptor signaling complexes," *Protein Science*, 2:1785–1797 (1993).

Fukushigi et al., "Localization of a Novel v–erbB–Related Gene, c–erbB–2, on Human Chromosome 17 and Its Amplification in a Gastric Cancer Cell Line," *Mol. Cell. Biol.* 6:955–58 (1986).

Gazit et al., "Tyrphostins. 1. Systhesis and Biological Activity of Protein Tyrosine Kinase Inhibitors," *J. Med. Chem.*, 32:2344–2352 (1989).

Gazit et al., "Tyrphostins. 2. Heterocyclic and α–Substitued Benzylidenemalononitrile Tyrphostins as Potent Inhibitors of EGF Receptor and ErbB2/neu Tyrosine Kinases," *J. Med. Chem.*, 34:1896–1907 (1991).

Gazit et al., "Tyrphostins. 3. Structure–Activity Relationship Studies of α–Substituted Benzylidenemalononitrile 5–S–Aryltyrphostins" *J. Med. Chem.* 36:3556–3564 (1993).

Geurin et al., "Overexpression of Either c–myc or c–erbB–2/neu Proto–Oncogenes in Human Breast Carcinomas: Correlation with Poor Prognosis," *Oncogene Res.* 3:21–31 (1988).

Gottardis et al., "Estradiol–Stimulated Growth of MCF–7 Tumors Implanted in Athymic Mice: A Model to Study the Tumoristatic Action of Tamoxifen", *J. Steroid Biochem.* 30:331–314 (1988).

Hale et al., "Prognostic value of epidermal growth factor receptor expression in cervical carcinoma", *J. Clin. Pathol.* 46:149–153 (1993).

Hanks et al., "The Protein Kinase Family: Conserved Features and Deduced Phylogeny of the Catalytic Domains," *Science* 241:42–52 (1988).

Harris et al., "Breast Cancer (First of Three Parts)", *New England J. of Medicine* 327:319–328 (1992).

Holmes et al., "Identification of Heregulin, a Specific Activator of p185$^{erB2}$," *Science* 256:1205–10 (1992).

Huang et al., "Tyrosine Kinase–Depednent Suppression of a Potassium Channel by the G Protein–Coupled m1 Muscarinic Acetylcholine Receptor", *Cell* 75:1145–1156 (1993).

Hunter and Cooper, "Viral Oncogenes and Tyrosine Phosphorylation," *The Enzymes* vol. 17 (eds. Boyer and Krebs) pp. 191–246 (Academic Press 1986).

Jackman et al., "ICI D1694, a Quinazoline Antifolate Thymidylate Synthase Inhibitor That Is a Potent Inhibitor of L1210 Tumor Cell Growth In Vitro and in Vivo: A New Agent for Clinical Study," *Cancer Research* 51:5579–5586 (1981).

Jaehne et al., "Expression of Her2/neu Oncogene Product p185 in Correlation to Clinicopathological and Prognostic Factors of Gastric Carcinoma," *J. Cancer Res. Clin. Oncol.* 118:474–79 (1992).

Jones et al., "Quinazoline Antifolates Inhibiting Thymidylates Synthase: Variation of the Amino Acid," *J. Med. Chem.* 29:1114–1118 (1986).

Karameris et al., "Expression of Epidermal Growth Factor (EGF) and Epidermal Growth Factor Receptor (EGFR) in Gastric and Colorectal Carcinomas, An Immunohistological Study of 63 Cases", *Path. Res. Pract.* 189:133–137 (1993).

Kaur et al., "Tyrphostin Induced Growth Inhibition: Correlation With Effect on p210bcrabl Autokinase Activity in K562 Chronic Myelogenous Leukemia," *Anti–Cancer Drugs* 5:213–222 (1994).

King et al., "Site–Specific Dephosphorylation and Deactivation of the Human Insulin Receptor Tyrosine Kinase by Particulate and Soluble Phosphotyrosyl Protein Phosphates," *Biochem. J.* 275:413–418 (1991).

King et al., "Ligand–independent tyrosine phosphorylation of EGF receptor and the erbB–2/neu proto–oncogene product is induced by hyperosomotic shock," *Oncogene* 4:13–18 (1989).

Koenders et al., "Epidermal growth factor receptor and prognosis in human breast cancer: a prospective study", *Breast Cancer Research and Treatment* 25:21–27 (1993).

Kokai et al., "Synergistic Interaction of p185c–neu and the EGF Receptor Leads to Transformation of Rodent Fibrobalsts," *Cell* 58: 287–92 (1989).

Korzeniewski and Callewaert, "An Enzyme–Release Assay for Natural Cytotoxicity[1]," *J. Immunol. Methods*, 64:313 (1983).

Kraus et al., "Isolation and Characterization of ERBB3, a third member of the ERBB/epidermal growth factor receptor family: Evidence for overexpression in a subset of human mammary tumors", *Proc. Natl. Acad. Sci. U.S.A.* 86:9193–9197 (1989).

Kraus et al., "Demonstration of ligand–dependent signaling by the erbB–3 tyrosine kinase and its constitutive activation in human breast tumor cells", *Proc. Natl. Acad. Sci. U.S.A.* 90:2900–2904 (1993).

Kuo et al., "Effects of Signalling Transduction Modulators on the Transformed Phenotypes in v–H–ras–transformed NIH 3T3 cells," *Cancer Letters* 74:197–202 (1993).

Lee and Skibo, "Active–Site–Directed Reductive Alkylation of Xanthine Oxidase by Imidazo[4,5–g] quinazoline–4,9–diones Functionalized With a Leaving Group," *Biochemistry* 26(23):7355–7362 (1987).

Lemoine et al., "The erbB–3 Gene In Human Pancreatic Cancer," *Journal of Pathlogy* 168:269273 (1992).

Lemoine et al., "Expression of the ERBB3 Gene Product in Breast Cancer," *Br. J. Cancer* 66:116–1121 (1992).

Lemus et al., "Studies of Extended Quinone Methides. synthesis and Physical Studies of Purine–like Monofunctional and bifunctional Imidazo[4,5–g] quinazoline Reductive Alkylating Agents," *J. Org. Chem.* 54:3511–3518 (1989).

Levitzki, "Tyrphostins: tyrosine kinase blockers as novel antiproliferative agents and dissectors of signal transduction," *The FASEB J.* 6:3275–3282 (1992).

Ley and Seng, "Synthesen unter Verwendung von Benzofuroxan", *Synthesis* 1975:415–422 (1975).

Lupu et al., "Direct Interaction of a Ligand for the erbB2 Oncogene Product with the EGF Receptor and p185erbB2," *Science* 249:1552–55 (1990).

Lupu et al., "Characterization of a growth factor that binds exclusively to the erbB–2 receptor and induces cellular responses," *Proc. Natl. Acad. Sci. U.S.A.* 89:2287–91 (1992).

Lyall et al., "Tyrphostins Inhibit Epidermal Growth Factor (EGF)–Receptor Tyrosine Kinase Activity in Living Cells and EGF–stimulated Cell Proliferation," *J. Bio. Chem.*, 264:14503–14509 (1989).

Mafiakowski and Carroll, "A Novel of Cell Surface Receptors With Tyrosine Kinase–Like Domain," *J. Biol. Chem.* 267:26181–26190 (1992).

MaGuire, "A New Series of PDGF Receptor Tyrosine Kinase Inhibitors: 3–Substituted Quinoline Derivatives," *J. Med. Chem.* 37:2129–2131 (1994).

Marshall, "Search for a Killer: Focus Shifts from Fat to Hormones", *Science* 259:618–621 (1993).

Maxwell et al., "$^{19}$F Nuclear Magnetic Resonance Imaging of Drug Distribution in Vivo: The Disposition of an Antifolate Anticancer Drug in Mice," *Magnetic Resonance in Medicine* 17:189–196 (1991).

McCann et al., "c–erbB–2 Oncoprotein Expression in Primary Human Tumors," *Cancer* 65:88–92 (1990).

Mini et al., "Cytotoxic Effects of Folate Antagonists against Methotrexate–resistant Human Leukemic Lymphoblast CCRF–CEM Cell Lines," *Cancer Research* 45:325–330 (1985).

Mossman, "Rapid Colorimetric Assay for Cellular Growth and Survival: Application to Proliferation and Cytotoxicity Assays," *J. Immunol. Methods* 65:55–63 (1983).

Osherov et al., "Selective Inhibition of the Epidermal Growth Factor and HER2/Neu Receptors by Tyrphostins," *J. Bio. Chem.*, 268:11134–11142 (1993).

Ozzello and Sordat, "Behavior of Tumors Produced by Transplantation of Human Mammary Cell Lines in Athymic Nude Mice", *Eur. J. Cancer* 16:553–559 (1980).

Osborne et al., "Effects of Estrogens and Antiestrogens on Growth of Human Breast Cancer Cells in Athymic Nude Mice," *Cancer Res.*, 45:584–590 (1985).

Peles et al., "Isolation of the Neu/HER–2 Stimulatory Ligand: A 44 kd Glycoprotein That Induces Differentiation of Mammary Tumor Cells," *Cell* 69:205–216 (1992).

Peterson and Barnes, "Genistein and Biochanin A Inhibit the Growth of Human Prostate Cancer Cells but not Epidermal Growth Factor Receptor Tyrosine Autophosphorylation", *The Prostate* 22:335–345 (1993).

Phillips and Castle, "Quino[1,2–c]quinazolines. I. Synthesis of Quino[1,2–c]quinazolinium Derivatives and the Related Indazolo[2,3–a]quinoline Derivatives as Analogs of the Antitumor Benzo[c]phenanthridine Alkaloids," *J. Heterocyclic Chem.* 17(19):1489–1596 (1980).

Pillemer et al., "Insulin Dependence of Murine Lymphoid T–Cell Leukemia," *Int. J. Cancer* 50:80–85 (1992).

Plowman et al., "Heregulin induces tyrosine phosphorylation of HER4/p180$^{erbB4}$", *Nature* 366:473–475 (1993).

Plowman et al., "Molecular cloning and expression of an additional epidermal growth factor receptor–related gene", *Proc. Natl. Acad. Sci. U.S.A.* 87:4905–4909 (1990).

Plowman et al., "Ligand–specific activation of HEr4/p180$^{erbB4}$, a fourth member of the epidermal growth factor receptor family", *Proc. Natl. Acad. Sci., USA* 90:1746–1740 (1993).

Poller et al., *J. Path.* (1992) in press Poller et al., "Production and Characterization of a Polyclonal Antibody to the c–erbB–3 Protein: Examination of c–erbB–3 Protein Expression in Adenocarcinomas", *J. Pathology* 168:275–280 (1992).

Poller et al., "Production and Characterization of a Polyclonal Antibody to the c–erbB–3 Protein: Examination of a c–erbB–3 Protein Expression in adenocarcinomas," *Journal of Pathology*, 168:275–280 (1992).

Posner et al., "Kinetics of Inhibition by Tryphositins of the Tyrosine Kinase Activity of the Epidermal Growth Factor Receptor and Analysis by a New Computer Program," *Molecular Pharmacology* 45:673–683 (1993).

Reece et al., "Pharmacokinetics of Trimetrexate Administered by Five–Day Continuous Infusion to Patients with Advanced Cancer," *Cancer Research* 47(11):2996–2999 (1977).

Rendu et al., "Inhibition of Platelet Activation by Tyrosine Kinase Inhibitors," *Biochem. Pharm.*, 44(5):881–888 (1992).

Rygaard and Povlsen, "Heterotransplantation of a Human Malignant Tumour to 'Nude' Mice", *Acta path. microbiol. scand.* 77:758–760 (1969).

Sandias et al., "Expression of the c–erb–B–3 Gene Product in Gastric Cancer," *Int. J. Cancer* 54:935–940 (1993).

Sauro and Thomas, "Decreased Sensitivity of Aorta From Hypertensive Rats To Vasorelaxation by Tyrphostin," *Life Sciences* 53:371–376 (1993).

Sauro and Thomas, "Tyrphostin Attenuates Platelet–Derived Growth Factor–Induced Contraction in Aortic Smooth Muscle Through Inhibition of Protein Tyrosine Kinase(s)," *J. Phaarm. and Experimental Therapeutics* 267(3):119–1125 (1993).

Schlessinger, "Signal transduction by allosteric receptor oligomerization", *Trends Biochem. Sci.* 13:443–447 (1988).

Schlessinger and Ullrich, "Growth Factor Signalling by Receptor Tyrosine Kinases", *Neuron* 9:383–391 (1992).

Scott et al., "p185$^{HER2}$ Signal Transduction in Breast Cancer Cells", *J. Bio. Chem.* 266(22):14300–14305 (1991).

Sculier et al., *Cancer Immunol. and Immunother.* 23:A65 (1986).

Seibert et al., "Clonal Variation of MCF–7 Breast Cancer Cells In Vitro and in Athymic Nude Mice," *Cancer Res.*, 43:2223–2239 (1983).

Semba et al., "A v–erbB–related protoncogene, c–erbB–2, is distinct from the c–erbB–1/epidermal growth factor–receptor gene and is amplified in a human salivary gland adenocarcinoma," *Proc. Natl. Acad. Sci. U.S.A.* 82:6497–6501 (1985).

Shafie and Grantham, "Role of Hormones in Growth and Regression of Human Breast Cancer Cells (MCF–7) Transplanted into Athymic Nude Mice", *J. Natl Cancer Institute* 67(1):51–56 (1981).

Shing et al., "Betacellulin: A Mitogen from Pancreatic β Cell Tumors," *Science* 259:1604–1607 (1993).

Sikora and Grzelakowska–Sztabert, "Quinazoline CB 3717 and CB 3703 Inhibition of Folate Retention and Metabolism in Ehrlich Ascites Carcinoma Cells and Some Organs of the Host–Mouse," *Cancer Letters* 23:289–295 (1984).

Sikora et al., "Development of an Assay for the Estimation of $N^{10}$–Propargyl–5, 8–dideazafolic Acid Polyglutamates in Tumor Cells," *Analytical Biochem.* 172:344–355 (1988).

Slamon et al., "Human Breast Cancer: Correlation of Relapse and Survival with Amplification of the HEr–2/neu Oncogene", *Science* 235:177–185 (1987).

Slamon et al., "Studies of the HER–2/neu Proto–oncogene in Human Breast and Ovarian Cancer", *Science* 244:707–712 (1989).

Sliwkowski et al., "Coexpression of erbB2 and erbB3 Proteins Reconstitutes a High Affinity Receptor for Heregulin", *J. Biol. Chem.* 269:14661–14665 (1994).

Stern et al., "EGF–Stimulated Tyrosine Phosphorylation of $p185^{neu}$: a potential model for receptor interactsions," *The EMBO Journal* 7:995–1001 (1988).

Ullrich and Schlessinger, "Signal Transduction by Receptors with Tyrosine Kinase Activity", *Cell* 61:203–212 (1990).

Wada et al., "Anti–receptor antibodies reverse the phenotype of cells transformed by two interacting proto–oncogene encoded receptor proteins", *Oncogene* 5:489–495 (1990).

Warri et al., "Estrogen Suppression of erbB2 Expression is Associated with Increased Growth Rate of ZR–75–I Human Breast Cancer Cells In Vitro and in Nude Mice", *Int. J. Cancer* 49:616–623 (1991).

Watanabe, "Recombinant Human Betacellulin," *J. Biol. Chem.* 269:9966–9973 (1994).

Wen et al., "Neu Differentiation Factor: A Transmembrane Glycoprotein Containing an EGF Domain and an Immunoglobulin Homology Unit," *Cell* 69:559–72 (1992).

Weiner et al., "Expression of neu Gene–encoded Protein ($P185^{neu}$) in Human Non–small Cell Carinomas of the Lung," *Cancer Res.* 50:421–425 (1990).

Wolbring et al., "Inhibition of GTP–utilizing Enzymes by Tyrphostins," *J. Biol. Chem.* 269(36):22470–22472 (1994).

Yokota et al., "Cromoglycate Treatment of Patient with Hyperimmunoglobulinaemia E Syndrome," *Lancet* 1:765–767 (1986).

Yoneda et al., "The Antiproliferative Effects of Tyrosine Kinase Inhibitors Typhostins on a Human Squamous Cell Carcinoma in Vitro and in Nude Mice," *Cancer Research*, 51:4430–4435 (1991).

Zeillinger et al., "EGF-R and Steroid Receptors in Breast Cancer: A Comparison with Tumor Grading, Tumor Size, Lymph Node Involvement, and Agen", *Clin. Biochem.* 26:221–227 (1993).

Zhau et al., "Amplification and Expression of the c–erb B–2/neu Proto–Oncogene in Human Bladder Cancer," *Mol. Carcinog.* 3:354–57 (1990).

ASSAY FOR AGENTS ACTIVE IN PROLIFERATIVE DISORDERS

FIELD OF THE INVENTION

The present invention relates generally to the fields of biology, chemistry, biochemistry, molecular biology and medicine and more specifically to the field of cellular signal transduction.

BACKGROUND OF THE INVENTION

The following is a description of background information, none of which is admitted to be prior art to the claimed invention.

Receptor tyrosine kinases belong to a family of transmembrane proteins and have been implicated in cellular signaling pathways. The predominant biological activity of some receptor tyrosine kinases is the stimulation of cell growth and proliferation, while other receptor tyrosine kinases are involved in arresting growth and promoting differentiation. In some instances, a single tyrosine kinase can inhibit, or stimulate, cell proliferation depending on the cellular environment in which it is expressed. (Schlessinger, J. and Ullrich, A., Neuron, 9(3):383–391, 1992.)

Receptor tyrosine kinases contain at least seven structural variants. All of the receptor tyrosine kinases are composed of at least three domains: an extracellular glycosylated ligand binding domain, a transmembrane domain and a cytoplasmic catalytic domain that can phosphorylate tyrosine residues. Ligand binding to membrane-bound receptors induces the formation of receptor dimers and allosteric changes that activate the intracellular kinase domains and result in the self-phosphorylation (autophosphorylation and/or transphosphorylation) of the receptor on tyrosine residues. A possible role for receptor heterodimerization is described in Carraway III and Cantley, Cell 78:5–8 (1994).

Receptor phosphorylation stimulates a physical association of the activated receptor with target molecules. Some of the target molecules are in turn phosphorylated, which transmits the signal to the cytoplasm. For example, phosphorylation of phospholipase activates this target molecule to hydrolyze phosphatidylinositol 4,5-bisphosphate, generating two secondary signal transducing molecules: inositol triphosphate, which causes release of stored intracellular calcium, and diacylglycerol, which is the endogenous activator of a serine/threonine kinase, protein kinase C.

Other target molecules are not phosphorylated, but assist in signal transmission by acting as docking or adapter molecules for secondary signal transducer proteins. For example, receptor phosphorylation and the subsequent allosteric changes in the receptor recruit the Grb-2/SOS complex to the catalytic domain of the receptor where its proximity to the membrane allows it to activate ras (reviewed in Schlessinger, J. and Ullrich, A., Neuron, supra).

The secondary signal transducer molecules generated by activated receptors result in a signal cascade that regulates cell functions such as cell division or differentiation. Reviews describing intracellular signal transduction include Aaronson, S. A., Science, 254:1146–1153, 1991; Schlessinger, J., Trends Biochem. Sci., 13:443–447, 1988; and Ullrich, A., and Schlessinger, J., Cell, 61:203–212, 1990.

Various cell proliferative disorders have been associated with defects in different signaling pathways mediated by receptor tyrosine kinases. According to Aaronson, S. A., supra:

Signaling pathways that mediate the normal functions of growth factors are commonly subverted in cancer.

Examples of specific receptor tyrosine kinases associated with cell proliferative disorders include, platelet derived growth factor receptor (PDGFR), epidermal growth factor receptor (EGFR), and HER2 (HER2). The gene encoding HER2 (her-2) is also referred to as neu, and c-erbB-2 (Slamon, D. J., et al., Science, 235:177–182, 1987).

HER2/neu gene amplification has been linked by some investigators to neoplastic transformation. For example Slamon et al., supra, (hereby incorporated by reference herein in its entirety including any drawings) asserts:

The Her-2/neu oncogene is a member of the erB-like oncogene family, and is related to but distinct from the epidermal growth factor receptor. The gene has been shown to be amplified in human breast cancer cells.

According to Scott et al., supra, (hereby incorporated by reference herein in its entirety including any drawings):

Amplification and/or overexpression of HER2/neu has been detected in gastro-intestinal, nonsmall cell lung, and ovarian adenocarcinomas and occurs in a significant fraction of primary human breast cancers where it correlates with regionally advanced disease, increased probability of tumor recurrence, and reduced patient survival. (Citations omitted).

Publications discussing EGFR and cancer include Zeillinger et al., Clin. Biochem. 26:221–227, 1993; where it is asserted:

Increased expression of this receptor [EGFR] has been found in various malignancies. In carcinomas of the cervix, ovaries, esophagus, and stomach, positive EGF-R status is definitely associated with the aggressiveness of the tumor.

With regard to breast cancer the importance attached to the determination of EGF-R has been confirmed by reports by several groups on the positive correlation between EGF-R and relapse-free interval, as well as overall survival. (Citations omitted.)

Other references discussing cancer and EGFR include Karameris et al., Path. Res. Pract. 189:133–137, 1993; Hale et al., J. Clin. Pathol. 46:149–153, 1993; Caraglia et al., Cancer Immunol. Immunother. 37:150–156, 1993; and Koenders et al., Breast Cancer Research and Treatment 25:21–27, 1993); these references are hereby incorporated by reference herein in their entirety including any drawings.

Compounds able to inhibit the activity of receptor tyrosine kinases have been mentioned in various publications. For example, Gazit et al., J. Med. Chem. 34:1896–1907 (1991), examined the receptor tyrosine kinase inhibitory effect of different tyrphostins. According to Gazit:

Among the novel tyrphostins examined we found inhibitors which discriminate between the highly homologous EGF receptor kinase (HER1 and ErbB2/neu kinase (HER2). These findings may lead to selective tyrosine kinase blockers for the treatment of diseases in which ErbB2/neu is involved.

In a later publication Gazit et al., J. Med. Chem. 36:3556–3564 (1993) describe tyrphostins having a S-aryl substituent in the 5 position. According to Gazit:

We find that these compounds are potent blockers of EGFR kinase and its homolog HER-2 kinase. Interestingly, we find that certain S-aryltyrphostins discriminate between EGFR and HER-2 kinase in favor of the HER-2 kinase domain by almost 2 orders of magnitude. When examined in intact cells it was found that these selective S-aryltyrphostins are equipotent in inhibiting EGF dependent proliferation of NIH 3T3 harboring either the EGF receptor or the chimera EGF/neu HER1-2.

Osherov et al., *Journal of Biological Chemistry* 268:11134, 1993, mentions the development of two groups of tyrphostins:

one is highly selective in inhibiting HER1 [EGFR] as compared with HER2 kinase activity, and the other is highly selective in inhibiting HER2 activity compared with HER1 kinase activity.

Additional methods and compositions for inhibiting cell proliferative disorders are described in U.S. patent application Ser. No. 08/207,933, filed Mar. 7, 1994, (hereby incorporated by reference herein in its entirety including any drawings).

HER3 and HER4 have also been studied. The molecular cloning and expression of HER3 is described in Plowman et al., *PNAS* 87:4905–4909 (1990) (hereby incorporated by reference herein in its entirety including any drawings). The production and characterization of a polyclonal antibody to the HER3 protein in order to study the HER3 protein expression in adenocarcinomas is described in Poller et al., *Journal of Pathology*, 168:275–280 (1992).

The ligand-dependant signalling by the HER3 tyrosine kinase and its constitutive activation in human breast tumor cells is said to be demonstrated in Kraus et al., *PNAS*, 90:2900–2904 (1993) (hereby incorporated by reference herein in its entirety including any drawings). The co-expression of HER2 and HER3 proteins is said to reconstitute a high affinity receptor for heregulin in Sliwkowski et al., *The Journal of Biological Chemistry*, 269:14661–14665 (1994) (hereby incorporated by reference herein in its entirety including any drawings).

The ligand specific activation of HER4 is described in Plowman et. al, *PNAS* 90:1746–1750 (1993) (hereby incorporated by reference herein in its entirety including any drawings). The specific ligand for HER4 termed heregulin is described in Plowman et al., *Nature* 366:473–475 (1993), incorporated herein by reference in its entirety including any drawings. The purification of a protein that induces differentiation of human breast cancer cells and stimulates the tyrosine phosphorylation of the HER4 encoded protein is described in Culouscou et al., *The Journal of Biological Chemistry* 268:18407–18410 (1993).

SUMMARY OF THE INVENTION

The present invention relates to methods of assaying for agents useful for inhibiting cell proliferative disorders. The described methods are particularly useful for detecting agents which inhibit cell proliferative disorders characterized by over-activity and/or inappropriate expression of a receptor tyrosine kinase such as HER2.

Methods to screen for agents or compounds which can be used to inhibit either HER2, or HER4 activity, preferably HER2/HER3, HER2/HER4, or HER3/HER4 heterodimer activity are also provided. The described methods and agents are particularly useful for treating cell proliferative disorders, such as cancers characterized by over-activity or inappropriate activity of HER2, HER3 or HER4.

In addition to use as therapeutics, additional uses of the agents include use for in vitro studies to determine the mechanism of action of receptor tyrosine kinases, preferably HER2 or HER3 or HER4; use as lead compounds to design and screen for additional compounds having receptor tyrosine kinase inhibitory activity; and use to help diagnose the role of a receptor tyrosine kinase in a cell proliferative disorder. For example, using standard assays, the active site of the kinase acted upon by any one of the compounds described herein may be determined, and other compounds active at the same site determined.

The invention is based upon a recognition of the ability of using the functional relationship between HER4 or HER3 and HER2. It is further relevant to this invention that HER4 - or HER3 mediate phosphorylation of HER2. This may potentially occur via intracellular receptor crosstalk or receptor dimerization. The previously described ligands NDF/HRG (Hereregulin) and beta-cellulin mediate biological effects on certain cells not solely through HER2 or EGFR (in the case of beta-cellulin), but by means of a direct interaction with HER4 or HER3, or by way of an interaction with a HER2/HER4, HER2/HER3 or HER3/HER4 complex. Thus, recombinant cell lines for selective screening for HER2, HER3 or HER4 specific inhibitors are described herein. Particularly preferred are the ligand activated screening assays of the present invention which provide advantages over conventional constitutively activated assays. The HER2/HER4 heterodimer is preferred over the HER2/HER3 heterodimer for certain applications due to greater stability, better expression and better binding properties.

Thus, in a first aspect the invention features a method for identifying an agent for treatment of a proliferative disorder. The method includes assaying a potential agent for activity in inhibition of signal transduction by a HER2/HER3, HER2/HER4 or HER3/HER4 heterodimer.

In preferred embodiments, the heterodimer is provided within a cell; the inhibition is of the kinase activity of the heterodimer; and the disorder is a cancer, for example, leukemia, breast, pancreatic, ovarian, adenocarcinoma, and lung, colon, or gastric cancer. In other preferred embodiments, the inhibition of the signal transduction is by inhibition of the enzymatic activity of HER2 or HER4, for example, by agents with molecular weight less than 3000, preferably less than 1500 such as quinazolines, tyrphostins, quinolines, quinoxalines, and extracts from natural sources. Other agents may act by inhibiting the interaction of the components of the heterodimer, for example the interaction of HER2 and HER3, the interaction of HER2 and HER4, or the interaction of HER3 and HER4. Potential cells for use in the method include human breast adenocarcinoma, e.g., MCF7 cells, mouse fibroblast cells, e.g., G8 cells, and hematopoietic cells, such as FDCP, 32D or CEM cells, all of which are well known in the art and can be obtained from recognized sources or equivalents from such sources.

In a more preferred embodiment, the cell used in the assay includes a recombinant nucleic acid encoding at least one or more of HER2, HER3 or HER4 and the method includes providing a ligand which initiates the signal transduction of the HER2/HER3, HER2/HER4 or HER3/HER4 heterodimers. It is the action of the ligand which is preferably inhibited by the agent. Such a ligand includes beta-cellulin or heregulin and the agent is preferably contacted with the cell prior to contact of the cell with the ligand. The assay step may include detection of the level of phosphorylation of at least one of the HER2, HER3 or HER4.

By "identifying" is meant one or more chemical agents are tested in the method of the invention to determine their activity in inhibition of signal transduction. Those agents which inhibit by at least 50% (preferably 90%, more preferably 95%) the level of signal transduction in the absence of such an agent are potentially useful for treatment of a proliferative disorder. Thus, the identifying may encompass a single test of a single agent or a plurality of tests of a plurality of agents. The level of signal transduction can be measured in a variety of ways well known to those skilled in the art. For example, the presence or amount of phosphorylation of a given protein (such as a HER2, HER3 or HER4 protein) can be used to measure signal transduction.

By "proliferative disorder" is meant a state in an organism, e.g., a human, which is recognized as abnormal by members of the medical community that relates to cell proliferation. An abnormal state is characterized by a level of a property that is statistically different from the level observed in organisms not suffering from the disorder. Examples of disorders encompassed by the present invention include cancers and hyperproliferative disorders such as psoriasis and nuerofibromatosis. Cell proliferation refers to growth or extension by multiplication of cells and includes cell division. The rate of cell proliferation may be measured by counting the number of cells produced in a given unit of time.

The term "assay" is used in its well recognized form to mean performing of a protocol on an agent to determine the activity of that agent in inhibition of signal transduction.

By "inhibition" is meant that the level of signal transduction is reduced at least 50% (preferably at least 90%, more preferably at least 95%) by the agent in the assay performed.

By "signal transduction" is meant the passage of a molecular signal from the HER2/HER3, HER2/HER4, or HER3/HER4 heterodimers to one or more molecules in the signal cascade within the cell. For example, such a signal may be transduced dependent upon the level of phosphorylation of the HER2/HER3, HER2/HER4 or HER3/HER4 heterodimers. Thus, an agent which inhibits phosphorylation of the heterodimers will reduce the ability of those heterodimers to affect signal transduction. If the agent prevents interaction of the components of the heterodimers that also may prevent signal transduction either directly or by prevention of phosphorylation of the components of the heterodimer. As noted above, other molecules which may assist in signal transmission may be blocked by agents of this invention and thus reduce signal transduction.

A "heterodimer" is a molecule containing at least two different components generally in a one to one ratio. In the present case, each heterodimer contains one molecule of HER2 and one molecule of either HER3 or HER4, or one molecule of HER3 and one molecule of HER4. It is this heterodimer that is active in signal transduction. Such heterodimers have been determined to be responsible for signal transduction and may generally only be formed within a cellular format and thus the assay is preferably performed within a cell as noted above. These heterodimers are able to enzymatically phosphorylate other molecules and/or themselves and this activity is termed the kinase activity. The components of heterodimers may be covalently or non-covalently associated and may be linked by a common bivalent ligand. For example, HER2 can phosphorylate itself or HER3 and HER4. Agents detected with the HER3/HER4 heterodimer assay include agents active with respect to HER4/HER4 homodimers.

The quinazolines, tyrphostins, quinolines, and quinoxalines referred to above include well known compounds such as those described in the literature. For example, representative publications describing quinazoline include Barker et al., EPO Publication No. 0 520 722 A1; Jones et al., U.S. Pat. No. 4,447,608; Kabbe et al., U.S. Pat. No. 4,757,072; Kaul and Vougioukas, U.S. Pat. No. 5,316,553; Kreighbaum and Comer, U.S. Pat. No. 4,343,940; Pegg and Wardleworth, EPO Publication No. 0 562 734 A1; Barker et al., *Proc. of Am. Assoc. for Cancer Research* 32:327 (1991); Bertino, J. R., *Cancer Research* 3:293–304 (1979); Bertino, J. R., *Cancer Research* 9(2 part 1):293–304 (1979); Curtin et al., *Br. J. Cancer* 53:361–368 (1986); Fernandes et al., *Cancer Research* 43:1117–1123 (1983); Ferris et al. *J. Org. Chem.* 44(2):173–178; Fry et al., *Science* 265:1093–1095 (1994); Jackman et al., *Cancer Research* 51:5579–5586 (1981); Jones et al. *J. Med. Chem.* 29(6):1114–1118; Lee and Skibo, *Biochemistry* 26(23):7355–7362 (1987); Lemus et al., *J. Org. Chem.* 54:3511–3518 (1989); Ley and Seng, *Synthesis* 1975:415–522 (1975); Maxwell et al., *Magnetic Resonance in Medicine* 17:189–196 (1991); Mini et al., *Cancer Research* 45:325–330 (1985); Phillips and Castle, *J. Heterocyclic Chem.* 17(19):1489–1596 (1980); Reece et al., *Cancer Research* 47(11):2996–2999 (1977); Sculier et al., *Cancer Immunol. and Immunother.* 23:A65 (1986); Sikora et al., *Cancer Letters* 23:289–295 (1984); Sikora et al., *Analytical Biochem.* 172:344–355 (1988); all of which are incorporated herein by reference in their entirety, including any drawings.

Quinoxaline is described in Kaul and Vougioukas, U.S. Pat. No. 5,316,553, incorporated herein by reference in its entirety, including any drawings.

Quinolines are described in Dolle et al., *J. Med. Chem.* 37:2627–2629 (1994); MaGuire, *J. Med. Chem.* 37:2129–2131 (1994); Burke et al., *J. Med. Chem.* 36:425–432 (1993); and Burke et al. *BioOrganic Med. Chem. Letters* 2:1771–1774 (1992), all of which are incorporated by reference in their entirety, including any drawings.

Tyrphostins are described in Allen et al., *Clin. Exp. Immunol.* 91:141–156 (1993); Anafi et al., *Blood* 82:12:3524–3529 (1993); Baker et al., *J. Cell Sci.* 102:543–555 (1992); Bilder et al., *Amer. Physiol. Soc.* pp. 6363–6143:C721–C730 (1991); Brunton et al., *Proceedings of Amer. Assoc. Cancer Rsch.* 33:558 (1992); Bryckaert et al., *Experimental Cell Research* 199:255–261 (1992); Dong et al., *J. Leukocyte Biology* 53:53–60 (1993); Dong et al., *J. Immunol.* 151(5):2717–2724 (1993); Gazit et al., *J. Med. Chem.* 32:2344–2352 (1989); Gazit et al., "*J. Med. Chem.* 36:3556–3564 (1993); Kaur et al., *Anti-Cancer Drugs* 5:213–222 (1994); Kaur et al., King et al., *Biochem. J.* 275:413–418 (1991); Kuo et al., *Cancer Letters* 74:197–202 (1993); Levitzki, A., *The FASEB J.* 6:3275–3282 (1992); Lyall et al., *J. Biol. Chem.* 264:14503–14509 (1989); Peterson et al., *The Prostate* 22:335–345 (1993); Pillemer et al., *Int. J. Cancer* 50:80–85 (1992); Posner et al., *Molecular Pharmacology* 45:673–683 (1993); Rendu et al., *Biol. Pharmacology* 44(5):881–888 (1992); Sauro and Thomas, *Life Sciences* 53:371–376 (1993); Sauro and Thomas, *J. Pharm. and Experimental Therapeutics* 267(3):119–1125 (1993); Wolbring et al., *J. Biol. Chem.* 269(36):22470–22472 (1994); and Yoneda et al., *Cancer Research* 51:4430–4435 (1991); all of which are incorporated herein by reference in their entirety, including any drawings.

The above-noted groups of compounds are believed to be particularly useful for screening in this assay and to be potentially useful in treatment of the noted cancers. Those in the art can use the assays described or equivalents of such assays for routine screening of such molecules to find those which are active in inhibition of the signal transduction pathway discussed above and thus useful for treatment of those cancers.

By "treatment" it is simply meant that the life expectancy of an individual affected with such a cancer will be increased or that one or more symptoms of the disease will be reduced.

The recombinant nucleic acid noted above is available to those of ordinary skill in the art and thus the cells can be readily constructed using routine experimentation and molecular biology techniques. In addition, the method for detecting levels of phosphorylation as one example of measurement of the signal transduction by the heterodimers are routine in the art.

In other aspects the invention features methods for treatment of the above noted cancers by the molecules identified in any of the screening assays of the present invention. In addition, the invention features novel compounds of the groups noted above which are identified by use of these methods. It also includes molecules which are derived by standard methodology from such agents when such agents are used as lead compounds.

Agents of this invention thus have a "therapeutic effect" which generally refers to either the inhibition, to some extent, of growth of cells causing or contributing to a cancerous disorder; or the inhibition, to some extent, of the production of factors (e.g., growth factors) causing or contributing to such a disorder. A therapeutic effect relieves to some extent one or more of the symptoms of the disorder. In reference to the treatment of a cancer, a therapeutic effect refers to one or more of the following: 1) reduction in tumor size; 2) inhibition (i.e., slowing to some extent, preferably stopping) of tumor metastasis; 3) inhibition, to some extent, of tumor growth; and/or 4) relieving to some extent one more or the symptoms associated with the disorder. Compounds with efficiency for treating leukemia can be identified as above, but rather than inhibiting metastasis, they may instead slow or decrease cell proliferation or growth.

When used as a therapeutic the compounds described herein are preferably administered with a physiological acceptable carrier. A physiological acceptable carrier is a formulation to which the compound can be added to dissolve it or otherwise facilitate its administration. Examples of physiological acceptable carriers include water, saline, physiologically buffered saline, cyclodextrins and PBTE:D5W (described below). Hydrophobic compounds are preferably administered using a carrier such as PBTE:D5W. An important factor in choosing an appropriate physiological acceptable carrier is choosing a carrier in which the compound remains active or the combination of the carrier and the compound produces an active compound. The compound may also be administered in a continuous fashion using a slow release formulation or a pump to maintain a constant or varying drug level in a patient.

By an "inhibitor" of a receptor tyrosine kinase is meant that the compound reduces to some extent the activity of HER2/HER3, HER2/HER4 or HER3/HER4. By "significantly inhibit" is meant the compound has an $IC_{50}$ less than 50 µm in an assay as described below.

In another aspect the invention features a method of treating a patient having a disorder characterized by overactivity of HER2/HER3, HER2/HER4 or HER3/HER4. The method involves administering to the patient a therapeutically effective amount of a compound able to significantly inhibit HER2/HER3, HER2/HER4 or HER3/HER4 activity as identified above.

In another aspect the invention features a method of screening for an agent that specifically or selectively inhibits a first receptor tyrosine kinase. The method involves assaying a potential agent for the ability to inhibit the activity of a heterodimer. One component of the heterodimer is catalytically inactive as an individual component and is capable of forming a heterodimer with the first receptor tyrosine kinase.

In preferred embodiments the first receptor tyrosine kinase is HER2 or HER4 and the heterodimer is HER2/HER3, HER2/HER4 or HER3/HER4. The second receptor tyrosine kinase may be a kinase defective HER2 or HER4. Those skilled in the art will recognize that HER3 is always inactive and that the heterodimers having HER3 will have another active component, such as HER2 or HER4.

By "specifically inhibits" is meant that the agent inhibits the kinase activity of a first component of the heterodimer (for example, a HER2 receptor tyrosine kinase) but not the kinase activity of another component capable of forming a heterodimer with the first component (for example, a HER4 receptor tyrosine kinase).

By "component" is meant an individual subunit that can form a heterodimer by associating or conjugating with another component. Individual component are well known to those skilled in the art and may be identified using conventional methodologies, for example by coimmunoprecipitation or chemical cross-linking.

By "catalytically inactive" is meant that the component or heterodimer has a reduced ability to transmit a signal, as may be measured by the ability to phos-phorylate or autophosphorylate. Examples of catalytically inactive components include kinase defective HER2 and HER4. Individual components may be studied in separate systems such as bacterial or insect expression systems well known to those skilled in the art.

By "associated" is meant that the two components are linked with each other, either directly or indirectly. Those skilled in the art are familiar with heterodimers and recognize that various relationships and mechanisms are sufficient for connecting two components into a heterodimer. The components of a heterodimer may be covalently or noncovalently associated or may be linked by a bivalent ligand.

Examples of receptor tyrosine kinases that are inactive as an individual component but that may be capable of forming an active heterodimer include KLG and ROR. Chou and Haman, *PNAS* 88:4897–4901 (1991); Mafiakowski and Carroll, *J. Biol. Chem.* 267:26181–26190 (1992).

In another aspect the invention features a method of screening for a compound or agent that specifically or selectively inhibits the activity of a receptor tyrosine kinase. The method involves providing a heterodimer in a cell, contacting the cell with the agent, providing a ligand that activates the heterodimer and detecting any change in the level of signal transduction in the cell. The heterodimer includes a first receptor tyrosine kinase that is active as an individual component conjugated to a second receptor tyrosine kinase that is inactive as an individual component and that is capable of forming a heterodimer with the first receptor tyrosine kinase. In preferred embodiments, the level of signal transduction is detected by measuring HER2 activity, for example by measuring phosphorylation of HER2 or a HER2 substrate.

In another aspect the invention provides a method that selectively inhibits the kinase activity of a heterodimer. One component of the heterodimer is catalytically inactive, for example as an individual component.

Other receptor tyrosine kinases that are inactive as an individual component can readily be identified by those skilled in the art and used form heterodimers for use in the screening assays of the present invention.

Other features and advantages of the invention will be apparent from the following description of the preferred embodiments thereof, and from the claims.

DESCRIPTION OF THE PREFERRED EMBODIMENTS

The present disclosure describes compounds and methods which can be used to inhibit receptor tyrosine kinase activity. The compounds and methods are preferably used in the treatment of cell proliferative disorders characterized by over-activity or inappropriate activity of a receptor tyrosine kinase. Different groups of heterodimer compounds are described.

The compounds described herein can differ in their selectivity. Selectivity, or selective inhibition refers to the ability of a compound to significantly inhibit the activity of a first receptor tyrosine kinase (e.g., HER2 or HER4) or heterodimer (e.g., HER2/HER3, HER2/HER4 or HER3/HER4) but not inhibit a second receptor tyrosine kinase (e.g., EGFR, or PDGFR) or heterodimer.

In general, it is preferred that a therapeutic compound be selective for a particular receptor tyrosine kinase. Receptor tyrosine kinases are important in many biological processes including cell growth, differentiation, aggregation, chemotaxis, cytokine release, and muscle contraction. Many of these events are mediated through different tyrosine kinase receptors. In addition, different tyrosine kinase receptors may be important for a particular biological function in different cell types. By developing selective inhibitors for a particular receptor tyrosine kinase, the potential for side effects of the compound is decreased. In those conditions where more than one receptor tyrosine kinase plays a role a compound which can inhibit both of these activities, but not other receptor kinases would be preferred.

Recent studies have identified two additional members of the EGFR/HER2 family of tyrosine kinase receptors, termed HER3 and HER4. Both of these receptors have been shown to interact directly with a soluble factor termed NDF, or heregulin (HRG) (Wen et al., 1992, *Cell* 69:559–72; Holmes et al., 1992 *Science* 256:1205–10; Plowman et al., 1993 *Nature* 366:473–5; Carraway et al., 1994 *J. Biol. Chem.* 269:14303–6). Furthermore, the presence of either HER3 or HER4 is necessary for HRG-dependent phosphorylation of HER2. One explanation for these findings is that HER2 forms a heterodimer with either HER3 or HER4, thereby generating a high-affinity binding site for HRG. Ligand binding to the heterodimeric receptor results in activation of the cytoplasmic kinase domains, leading to phosphorylation of the receptor complex and associated substrates. Previous reports of HER2 heterodimerization include the binding of EGF to the EGFR, resulting in activation of the EGFR kinase domain and cross-phosphorylation of HER2 (Kokai et al., 1989, *Cell* 58: 287–92; Stern et al., 1988, *EMBO J.* 7: 995–1001; King et al., 1989, *Oncogene* 4: 13–18).

Several lines of evidence demonstrate that HER3 lacks intrinsic tyrosine kinase activity. HER3 has alterations in four amino acid residues within its kinase homology domain that are highly conserved among all known kinases. This initial observation raised the possibility that HER3 is an inactive kinase. Recent studies on insect cells or bacteria that express recombinant HER3 have failed to show detectable kinase activity, confirming that HER3 is enzymatically inactive. However HER3 serves as an excellent substrate for phosphorylation by HER2 and presumably by EGFR. Since HER3 has an abundance potential tyrosine phosphorylation sites, it has been proposed that phosphorylated HER3 may function as a docking protein or an adaptor molecule for a number of downstream signalling molecules. Therefore, although catalytically inactive, HER3 may provide HER2 with both a ligand binding site and access to additional signal transduction pathways.

Similar to HER3, HER4 can also confer ligand responsiveness to HER2 and provides additional phosphotyrosine attachment sites. However, unlike HER3, HER4 contains intrinsic ligand regulated tyrosine kinase activity. Conceivably, ligand binding to a HER3/HER2 or HER4/HER2 heterodimers could result in distinct cellular effects. In this context, small molecules which specifically inhibit either HER2 or HER4 kinase activity could have distinct cellular effects and be useful for inhibiting the growth of certain diseased cells, such as specific subsets of cancer.

Activation of tyrosine kinase receptors is generally felt to be the result of ligand stimulated receptor dimerization, leading to activation of the cytoplasmic tyrosine kinase domain and transphosphorylation of the receptors within the dimer. However, since HER3 lacks tyrosine kinase activity, it is intriguing that HRG can induce phosphorylation of the HER3/HER2 heterodimer. Apparently, HER2 can be activated in the context of a single active catalytic domain. New approaches to designing recombinant cell lines to differentiate kinase specificity, and to screen for HER2, HER3 or HER4 specific inhibitors are now provided.

Assays

The present disclosure relates to the identification of specific compounds including to the classes and groups described herein which are useful in the present invention. Identification can be carried out by assaying the ability of a compound to inhibit receptor tyrosine kinase activity, and preferably, the ability of the compound to inhibit growth of cells having a receptor tyrosine kinase driven disorder. Such assays can be preformed as described in the art, or as described in the examples below.

These assays make use of heterodimers described above to allow specific detection of useful agents for treatment of cancers. Those in the art will recognize these assays are not limiting in this invention, and that equivalent assays are readily devised. In particular, those skilled in the art will recognize that other cell lines may be used that express the components of a heterodimer.

1. MCF7/HER2: MCF7 cells are derived from a human breast adenocarcinoma and contain low levels of HER2 and intermediate amounts of HER3 and HER4. Overexpression of recombinant HER2 in these cells result in little change in basal levels of tyrosine phosphorylation, but in a dramatic increase in HRG-induced tyrosine phosphorylation due to the generation of a high-affinity heterodimer of HER2/HER3 or HER2/HER4. These cells are useful for screening for nonspecific kinase inhibitors that are active on both the HER2 and HER4 kinases.

2. G8/HER4KA-Tag: G8 cells are mouse NIH3T3 fibroblasts which overexpress wild type recombinant rat neu. These cells express functional, active rat HER2 kinase. The normal rat receptor is activatable and has low basal kinase activity due to the absence of the activating mutation in the transmembrane domain. These cells can be transfected with a HER4 expression construct that has been rendered catalytically inactive. Kinase defective receptors can be generated by a lysine (K) to alanine (A) mutation in the ATP-binding domain in the cytoplasmic kinase domain. Alternatively, these kinase defective receptors may be generated by a mutation of a critical aspartate residue in the "DFG" motif in domain VII of the kinase. This motif along with a distal lysine residue is required for catalytic activity (Hanks et al., 198, *Science* 241: 42–52; Hunter and Cooper, in *The Enzymes* Vol. 17 (eds. Boyer and Krebs) pp. 191–246 (Academic Press 1986). This construct also contains 10 amino acids (YPYDVPDYAS)

(SEQ. I.D. NO. 1) at its C-terminus as an epitope tag. Cells selected to express this construct demonstrate HRG-induced tyrosine phosphorylation of HER2 and HER4 mediated by the HER2 kinase. This line is useful for screening for HER2 -specific kinase inhibitors.

3. NIH3T3/HER2KA/HER4: NIH3T3 cells will first be transfected with a catalytically inactive HER2 expression construct, analogous to the kinase defective mutants of HER4 described above. These cells will then be transfected with a second vector containing normal HER4 with the 10-amino acid epitope tag. These cells will also demonstrate HRG-induced tyrosine phosphorylation of HER2 and HER4, but mediated by the HER4 kinase. This line is useful for screening for HER4-specific kinase inhibitors.

Many hematopoietic cells are devoid of various members of the EGFR family (EGFR, HER2, HER3, HER4). Useful examples include FDCP, 32D and CEM cells. These cells provide a clean background in which to reconstitute specific receptor heterodimers and are therefore useful as specificity screens for inhibitors identified in the screens identified in the primary screens on MCF7/HER2, G8/HER4KA-Tag, and G8/HER2KA/HER4 cells. Adherent cells stick to plastic and make ideal reagents in high-throughput screens.

4. Hematopoietic cells FDCP, 32D, or CEM) transfected with HER2 and HER3-Tag. HER3-Tag is an expression construct containing full length HER3 with a 10-aa epitope tag. These cells can be selectively stimulated with HRG with subsequent HER2-mediated tyrosine phosphorylation of both HER2 and HER3. This line is used to define HER2 kinase specific inhibitors.

5. Hematopoietic cells (FDCP, 32D, or CEM) transfected with HER4-Tag and HER2KA. HER4-Tag is an expression construct containing full length HER4 with a 10-aa epitope tag. The HER2KA construct is described above and contains no kinase activity. These cells can be selectively stimulated with HRG with subsequent HER4-mediated tyrosine phosphorylation of both HER2 and HER4. This line is used to define HER4 kinase specific inhibitors.

6. Hematopoietic cells (FDCP, 32D, or CEM) transfected with HER4-Tag and HER3-Tag. These epitope tagged constructs are described above. These cells may be selectively stimulated with HRG with subsequent HER4mediated tyrosine phosphorylation of both HER3 and HER4. This line provides a potential alternate to line 5 and is used to define HER4 kinase inhibitors.

After identification of agents from the above cellular kinase-type assays, in vivo tests can be used to ensure utility for human therapy, e.g., as described below, for example, in vivo soft agar assays for heterodimer driven cancers.

Examples of cell lines which can be used to study the effect of a compound, for example in vitro or in animal models, include MCF7 cells or the ligand responsive G8/HER4-KA-TAG, and others well known in the art or which can be generated by standard methodology. One skilled in the can choose other suitable cell lines using standard techniques and the present application as a guide. For example, the diagnostic section described infra can be used to help determine whether a cell line (e.g., a tumor cell line) is driven by a tyrosine receptor kinase.

Animal model systems can also be used to further measure the therapeutic effect of a compound. Examples of suitable animal models include subcutaneous xenograft model and in situ mammary fat pad model.

1. Xenograft Model

The ability of human tumors to grow as xenografts in athymic mice (e.g., Balb/c, nu/nu) provides a useful in vivo model for studying the biological response to therapies for human tumors. Since the first successful xenotransplantation of human tumors into athymic mice by Ryaard and Povlsen (Rygaard, J. and Polvsen, C. O., *Acta Pathol. Microbial. Scand.*, 77:758–760, 1969.), many different human tumor cell lines (i.e., mammary, lung, genitourinary, gastrointestinal, head and neck, glioblastoma, bone, and malignant melanomas) have been transplanted and successfully grown in nude mice. Human mammary tumor cell lines, including MCF-7, ZR75-1, and MDA-MB-231, have been established as subcutaneous xenografts in nude mice (Warri, A. M., et al., *Int. J. Cancer*, 49:616–623, 1991; Ozzello, L. and Sordat, M., *Eur. J. Cancer*, 16:553–559, 1980; Osborne, C. K., et al., *Cancer Res.*, 45:584–590, 1985; Seibert, K., et al., *Cancer Res.*, 43:2223–2239, 1983).

To study the effect of anti-tumor drug candidates n heterodimer-expressing tumors, the tumor cells should preferably be able to grow in the absence of supplemental estrogen. Many mammary cell lines are dependent on estrogen for in vivo growth in nude mice (Osborne et al., supra), however, exogenous estrogen suppresses her2 expression in nude mice (Warri et al., supra, Dati, C., et al., *Oncogene*, 5:1001–1006, 1990). For example, in the presence of estrogen, MCF-7, ZR-75-1, and T47D cells grow well in vivo, but express very low levels of HER2 (Warri et al., supra, Dati, C., et al., *Oncogene*, 5:1001–1006).

The following type of xenograft protocol can be used: 1) implant tumor cells (subcutaneously) into the hindflank of five- to six-week-old female Balb/c nu/nu athymic mice; 2) administer the anti-tumor compound; 3) measure tumor growth by measuring tumor volume. The tumors can also be analyzed for the presence of a receptor such as HER2, HER3 or HER4, by Western and immunohisto-chemical analyses. Using techniques known in the art, one skilled in the art can vary the above procedures, for example through the use of different treatment regimes.

2. Mammary Fat Pad Model

The mammary fat pad model is particularly useful for measuring the efficacy of compounds which inhibit HER2, HER3, and HER4, because of the role HER2, HER3, and HER4 play in breast cancer. By implanting tumor cells directly into the location of interest, in situ models more accurately reflect the biology of tumor development than do subcutaneous models. Human mammary cell lines, including MCF-7, have been grown in the mammary fat pad of athymic mice (Shafie, S. M. and Grantham, F. H., *J. Natl. Cancer Instit.*, 67:51–56, 1981; Gottardis, M. M., et al., *J. Steroid Biochem.*, 30:311–314, 1988). For example the following procedure can be used: 1) MDA-MB-231 and MCF-7 cells transfected with HER2, HER3 and/or HER4 are implanted at various concentrations into the axillary mammary fat pads of female athymic mice; 2) the compound is administered; and 3) tumor growth is measured at various time points. The tumors can also be analyzed for the presence of a receptor such as HER2, HER3, and HER4 by Western and immunohisto-chemical analyses. Using techniques known in the art, one skilled in the art can vary the above procedures, for example through the use of different treatment regimes.

3. Further Analysis

Therapeutic compounds should be more potent in inhibiting receptor tyrosine kinase activity than in exerting a cytotoxic effect. A measure of the effectiveness and cell toxicity of a compound can be obtained by determining the therapeutic index: $IC_{50}/LD_{50}$. $IC_{50}$, the dose required to achieve 50% inhibition, can be measured using standard techniques such as those described herein. $LD_{50}$, the dosage which results in 50% toxicity, can also be measured by standard techniques, such as using an MTT assay as described by Mossman *J. Immunol. Methods* 65:55–63 (1983), by measuring the amount of LDH released (Korzeniewski and Callewaert, *J. Immunol. Methods* 64:313 (1983) ; Decker and Lohmann-Matthes, *J. Immunol. Methods* 115:61 (1988), or by measuring the lethal dose in animal models. Compounds with a large therapeutic index are preferred. The therapeutic index should be greater than 2, preferably at least 10, more preferably at least 50.

In addition to measuring tumor growth in the animal models, plasma half-life and biodistribution of the drug and metabolites in plasma, tumors, and major organs can be determined to facilitate the selection of drugs most appropriate for the inhibition of a disorder. Such measurements can be carried out, for example, using HPLC analysis. Compounds that show potent inhibitory activity in the screening assays but have poor pharmacokinetic characteristics can be optimized by altering the chemical structure and retesting. In this regard, compounds displaying good pharmacokinetic characteristics can be used as model.

Toxicity studies can also be carried out by measuring the blood cell composition. For example, toxicity studies can be carried out as follows: 1) the compound is administered to mice (an untreated control mouse should also be used); 2) blood samples are periodically obtained via the tail vein from one mouse in each treatment group; and 3) the samples are analyzed for red and white blood cell counts, blood cell composition, and the percent of lymphocytes versus polymorphonuclear cells. A comparison of results for each dosing regime with the controls indicates if toxicity is present.

At the termination of each study, further studies can be carried out by sacrificing the animals (preferably, in accordance with the American Veterinary Medical Association guidelines Report of the American Veterinary Medical Assoc. Panel on Euthanasia. *Journal of American Veterinary Medical Assoc.*, 202:229–249, 1993). Representative animals from each treatment group can then be examined by gross necropsy for immediate evidence of metastasis, unusual illness, or toxicity. Gross abnormalities in tissue are noted, and tissues are examined histologically. Compounds causing a reduction in body weight or blood components less preferred, as are compounds having an adverse effect on major organs. In general, the greater the adverse effect the less preferred the compound.

A cancer cell refers to various types of malignant neoplasms, most of which can invade surrounding tissues, and may metastasize to different sites, as defined by Stedman's Medical Dictionary 25th edition (Hensyl ed. 1990).

HER2, HER3 or HER4 driven disorders are characterized by over-activity or hyperphosphorylation of HER2, HER3 or HER4, respectively. For simplicity, just HER2 will be discussed, but the following also applies to HER3 and HER4 and the associated heterodimers. Over-activity of HER2 refers to either an amplification of the gene encoding HER2 or the production of a level of HER2 activity which can be correlated with a cell proliferative disorder (i.e., as the level of HER2 increases the severity of one or more of the symptoms of the cell proliferative disorder increases).

Activation of HER2 activity can result from several different events including: 1) ligand binding; 2) HER2 stimulation through transphosphorylation by activated EGFR; and 3) overexpression of her-2, encoding HER2 protein, can create a high abundance of HER2 resulting in ligand-independent dimerization. HER2 activity can be assayed by measuring one or more of the following activities: (1) phosphorylation of HER2; (2) phosphorylation of a HER2 substrate (e.g., $IP_3$ kinase, and PI 4-kinase, see Scott et al., *Journal of Biological* 22:14300, 1991); (3) activation of an HER2 adapter molecule; and (4) increased cell division. These activities can be measured using techniques described below and known in the art. For example, $IP_3$ kinase, and PI 4-kinase, activities can be assayed as described by Scott et al., supra, cell division can be assayed by measuring $^3H$-thymidine incorporation into DNA, and phosphorylation of HER2 can be assayed as described by Gazit et al., *J. Med. Chem.* 34:1896–1907, 1991, or as described in examples detailed below.

Treatment of patients suffering from a HER2 disorder is facilitated by first determining whether the cell proliferative disorder is characterized by an over-activity of HER2. After the disorder is identified, patients suffering from such a disorder can be identified by analysis of their symptoms by procedures well known to medical doctors. Such identified patients can then be treated as described herein.

HER2 driven disorders are typically cell proliferative disorders such as cancers. HER2 driven disorders appear to be responsible for a sub-population of different types of cancers. For example, as noted above, Slamon et al., found about 30% of breast cancer cells to have increased HER2 gene expression. Slamon et al., also found a correlation between her2 (c-erbB-2) amplification and poor patient prognosis.

The use of the present invention to treat breast cancer is preferred because of the prevalence and severity of breast cancer. Carcinoma of the breast is the most common cancer among women and their second leading cause of cancer death (Marshall, E., *Science* 259:618–621, 1993). The incidence of breast cancer has been increasing over the past several decades (Marshall, supra, and Harris, J. R., et al, *New Engl. J. Med.*, 327(5):319–328, 1992).

While specific note is made to breast cancers, increased HER2, HER3, or HER4 activity or gene expression has been associated with other types of cancers as noted above. The methods described herein can be used to identify the sub-populations of these different cancers which are characterized by over-activity of HER2, HER3 or HER4.

HER2 amplification or overexpression has been associated with numerous human malignancies. Studies of breast and ovarian carcinomas reveal a strong correlation between HER2 overexpression and poor clinical prognosis. (Slamon et al., *Science* 235:177–182 (1987) and *Science* 244:707–712 (1989) Overexpression of HER2 has also been correlated with other human carcinomas, including carcinoma of the stomach, endometrium, salivary gland, bladder, lung and gastric carcinoma (Yokota et al., 1986, Lancet 1:765–67; Fukushigi et al., *Mol. Cell. Biol.* 6:955–58 (1986); Yonemura et al., *Cancer Res.* 51:1034 (1991); Weiner et al., *Cancer Res.* 50:521–25 (1990: Geurin et al., *Oncogene Res.* 3:21–31 (1988); Semba et al., *Proc. Natl. Acad. Sci. U.S.A.* 82:6497–6501 (1985); Zhau et al., *Mol. Carcinog.* 3:354–57 (1990); McCann et al., *Cancer* 65:88–92 (1990); Jaehne et al. *J. Cancer Res. Clin. Oncol.* 118:474–79 (1992)). Amplified expression of the HER3 receptor has been observed in a wide variety of human adenocarcinomas. (Poller et al., *J. Path.*, 1992, in press; Krause et la., *Proc. Natl. Acad. Sci. U.S.A.* 86:9193–97

(1989)). Preliminary studies on HER4 mRNA expression identify highest expression in several human mammary adenocarcinoma cell lines (T-47D, MDa-MB-453, BT-474, and H3396), and in neuroblastoma (SK-N-MC), and pancreatic carcinoma (Hs766T) cell lines. Intermediate expression was detected in 3 additional mammary carcinoma cell line (MCF-7, MDA-MB-330, MDA-MB-361). Low or undetectable expression was found in other cell lines derived from carcinomas of the breast (MDB-MB-231, MDA-MB-157, MDa-MB-468, SK-BR-3), kidney (Caki-1, Caki-2, G-401), liver (SK-HEP1, HepG2), pancreas (PANC1, AsPC1, Capan-1), colon (HT-29), cervix (CaSki), vulva (A-41), ovary (PA1, Caov-3), melanoma (SK-MEL-28), or in a variety of leukemic cell lines.

Ligands

A specific ligand for HER2 remains elusive. Several reports have claimed the identification of a HER2 ligand; including gp30 (Lupu et al., Science 249:1552–55 (1990); Bacus et al., Cell Growth and Diff. 3:401–411 (1992)) which interacts with both EGFR and HER2, and others that are reported to be HER2-specific (Wen et al., Cell 69:559–72 (1992); Peles et al., Cell 69:205–16 (1992); Holmes et al., Science 256:1205–10 (1992); Lupu et al., Proc. Natl. Acad. Sci. U.S.A. 89:2287–91 (1992); Huang et al., J. Biol. Chem. 276 (11508–121 (1992)). The best characterized of these ligands are neu differentiation factor (NDF) purified and cloned from ras-transformed Rat1-EJ cells (Wen et al., Peles et al., supra), and its human homologues, termed hereregulins (HERG-α, -β1, -β2, -β3) (Holmes et al., supra). HRG/NDF proteins are 44–45 kDa glycoproteins which increase tyrosine phosphorylation of HER2 in MDA-MB-453 cells and not he EGF-receptor, and bind to HER2 on human breast cancer cells. In addition, some isoforms of these proteins (i.e., HRG-β1) induce differentiation of human mammary tumor cells to milk-producing, growth-arrested cells, whereas other isoforms (HRG-α) may function to stimulate proliferation of cultured human breast cancers cell monolayers.

Subsequent studies clearly demonstrate that HRG does not bind directly to HER2, but instead requires a direct interaction with HER3 or HER4 in order to activate the HER2 kinase.

Beta-cellulin has recently been described as a specific ligand with low affinity for the EGFR (Shing Y., et al., Science 259:1604–1607 (1993); Watanabe, T., J. Biol. Chem. 269:9966–9973 (1994)). More detailed analysis by us demonstrates it also interacts wit HER2 heterodimers with HER3 or HER4 in a manner analogous to HRG. Therefore either HRG or Beta-cellulin are suitable ligands for developing ligand inducible cell based screens. The ligands of the present invention bind and activate receptors of the HER family of receptors. Other ligands of the present invention have similar amino acid sequences and characteristic three dimensional structures and pattern of six conserved cysteine residues.

4. Administration Of Featured Compounds

The compounds of this invention can be administered to a patient alone, or in a pharmaceutical composition comprising the active compound and a carrier or excipient. The compounds can be prepared as pharmaceutically acceptable salts (i.e., non-toxic salts which do not prevent the compound from exerting its effect).

Pharmaceutically acceptable salts can be acid addition salts such as those containing hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate. (See, e.g., supra. PCT/US92/03736). Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Pharmaceutically acceptable salts can be prepared by standard techniques. For example, the free base form of the compound is first dissolved in a suitable solvent such as an aqueous or aqueous-alcohol solution, containing the appropriate acid. The salt is then isolated by evaporating the solution. In another example, the salt is prepared by reacting the free base and acid in an organic solvent.

Carriers or excipient can be used to facilitate administration of the compound, for example, to increase the solubility of the compound. Examples of carriers and excipients include calcium carbonate, calcium phosphate, various sugars or types of starch, cellulose derivatives, gelatin, vegetable oils, polyethylene glycols and physiologically compatible solvents. The compounds or pharmaceutical composition can be administered by different routes including intravenously, intraperitoneally, subcutaneously, and intramuscularly; orally, topically, or transmucosally.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, many small organic molecules may be directly administered intracellularly.

Pharmaceutical compositions suitable for use in the present invention include compositions wherein the active ingredients are contained in an effective amount to achieve its intended purpose. Determination of the effective amounts is within the capability of those skilled in the art, especially in light of the detailed disclosure provided herein.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained, for example by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

For any compound used in the method of the invention, the therapeutically effective does can be estimated initially from cell culture and animal models. For example, a dose can be formulated in animal models to achieve a circulating concentration range that includes the $IC_{50}$ as determined in cell culture. Such information can be used to more accurately determine useful doses in humans.

A preferred physiological carrier is PBTE:D5W. PBTE consists of a solution of 3% w/v benzyl alcohol, 8% w/v polysorbate 80, and 65% w/v polyethylene glycol (MW=300 daltons) in absolute ethanol. PBTE:D5W consists of PBTE diluted 1:1 in a solution of 5% dextrose in water.

The use of hydrophobic compounds can be facilitated by different techniques such as combining the compound with a carrier to increase the solubility of the compound and using frequent small daily doses rather than a few large daily doses. For example, the composition can be administered at short time intervals, such as by the methods described above or using a pump to control the time interval or achieve continuous administration. Suitable pumps are commercially available (e.g., the ALZET® pump sold by Alza corporation, and the BARD ambulatory PCA pump sold by Bard MedSystems).

The proper dosage depends on various factors such as the type of disease being treated, the particular composition being used, and the size and physiological condition of the patient. For the treatment of cancers the expected daily dose is between 1 to 2000 mg/day, preferably 1 to 250 mg/day, and most preferably 10 to 150 mg/day. Drugs can be delivered less frequently provided plasma levels of the active moiety are sufficient to maintain therapeutic effectiveness.

A factor which can influence the drug dose is body weight. Drugs should be administered at doses ranging from 0.02 to 25 mg/kg/day, preferably 0.02 to 15 mg/kg/day, most preferably 0.2 to 15 mg/kg/day. Alternatively, drugs can be administered at 0.5 to 1200 mg/m$^2$/day, preferably 0.5 to 150 mg/m$^2$/day, most preferably 5 to 100 mg/m$^2$/day. The average plasma level should be 50 to 5000 µg/ml, preferably 50 to 1000 µg/ml, and most preferably 100 to 500 µg/ml. Plasma levels may be reduced if pharmacological effective concentrations of the drug are achieved at the site of interest.

5. Diagnostic uses

Another use of the compounds described herein is to help diagnose whether a disorder is driven, to some extent, by a particular receptor tyrosine kinase. Some cancers may be driven by more than one receptor tyrosine cancers. For example, Wada et al., *Oncogene* 5:489–495, 1990, describing co-expression of EGFR and HER2.

A diagnostic assay to determine whether a particular cancer is driven by a specific receptor can be carried out using the following steps: 1) culturing test cells or tissues; 2) administering a compound which can inhibit one or more receptor tyrosine kinase; and 3) measuring the degree of growth inhibition of the test cells.

These steps can be carried out using standard techniques in light of the present disclosure. For example, standard techniques can be used to isolate cells or tissues and culturing in vitro or in vivo. An example of an in vitro assay is a cellular kinase assay as described below. An example of an in vivo assay is a xenograft experiment where the cells or tissues are implanted into another host such as a mouse.

Compounds of varying degree of selectivity are useful for diagnosing the role of a receptor tyrosine kinase. For example, compounds which inhibit more than one type of receptor tyrosine kinase can be used as an initial test compound to determine if one of several receptor tyrosine kinases drive the disorder. More selective compounds can then be used to further eliminate the possible role of different receptor tyrosine kinases in driving the disorder. Test compounds should be more potent in inhibiting receptor tyrosine kinase activity than in exerting a cytotoxic effect (e.g., an $IC_{50}/LD_{50}$ of greater than one). As noted above, $IC_{50}$ and $LD_{50}$ can be measured by standard techniques, such as described in the present application and using an MTT assay as described by Mossman supra, or by measuring the amount of LDH released (Korzeniewski and Callewaert, J. supra; Decker and Lohmann-Matthes, supra). The degree of $IC_{50}/LD_{50}$ of a compound should be taken into account in evaluating the diagnostic assay. Generally, the larger the ratio the more reliable the information. Appropriate controls to take into account the possible cytotoxic effect of a compound, such as treating cells not associated with a cell proliferative disorder (e.g., control cells) with a test compound, can also be used as part of the diagnostic assay.

EXAMPLES

Examples are provided below to illustrate different aspects and embodiments of the present invention. These examples are not intended in any way to limit he disclosed invention. Rather, they illustrate methodology by which agents can be readily identified by routine procedure to ensure that they have the desired activity.

These examples illustrate methods to screen exemplary compounds for the ability to inhibit receptor tyrosine kinases, such as HER2 and/or HER4. The following target cells may be used for cellular kinase assays: MCF7/HER2 cells and/or the transfected G8 cells or the transfected hematopoietic cells as described above. Growth assays may be carried out using the adherent MCF7/HER2 or transfected G8 cells.

The adherent cells are displaced into 96-well plates with test compounds plus or minus ligand. After 4 days the monolayers may be TCA-fixed then stained with sulphorhodamine B. The absorbance versus log drug concentration is plotted and $IC_{50}$ values are estimated. These adherent cells may be plated into soft agar with a test compound plus or minus ligand and colony growth is quantified 2 weeks later using an Omnicon colony counter. Unless otherwise stated receptor tyrosine kinases are assayed as described in this section. Example 1 describes a method to measure tyrosine phosphorylation on RTK's. Examples 2 and 3 describe methods to measure cell growth.

EXAMPLE 1.

HER2 or HER4-receptor Whole Cell Kinase Assay

HER2 or HER4 Kinase activity in whole cells is measured as described below:
Materials & Reagents
1) Heregulin or B-cellulin Ligand: stock concentration= 16.5 μM.
2) A monoclonal antibody recognizing HER2 or HER3 extracellular domain or recognizing a 10aa peptide tag from hemaglutinin.
3) Anti-Phosphotyosine antibody (polyclonal).
4) TAGO antibody: Goat anti-rabbit IgG horse radish peroxidase conjugate, TAGO, Inc., Burlingame, Calif.

| 5) | TBST buffer: | Tris-HCl, pH 7.2 | 50 mM |
| | | NaCl | 150 mM |
| | | Triton X-100 | 0.1% |
| 6) | HNTG stock | HEPES | 0.1M |
| | | NaCl | 0.75M |
| | | Glycerol | 50% |
| | | Triton X-100 | 0.1% |
| 7) | ABTS stock: | Citric Acid | 100 mM |
| | | $Na_2HPO_4$ | 250 mM |
| | | HCl, conc. | 0.5 pH |
| | | ABTS* | 0.5 mg/ml |

*(2,2'-azinobis(3-ethylbenzthiazolinesulfonic acid). Keep solution in dark at 4° C. until use.

8) Stock reagents of:
EDTA 100 mM pH 7.0
$Na_3VO_4$ 0.5M
$Na_4PO_7$ 0.2M

Procedure

The following protocol was used:

I. Pre-coat ELISA Plate

A. Coat ELISA plates (Corning, 96 well, Cat. #25805-96) with monoclonal antibody at 0.5 μg per well in PBS, 150 μl final volume/well, and store overnight at 4° C. Coated plates are good for up to 10 days when stored at 4° C.

B. On day of use, remove coating buffer and replace with blocking buffer (5% Carnation Instant Non-Fat Dry Milk in PBS). Incubate the plate, shaking, at room temperature (about 23° C. to 25° C.) for 30 minutes. Just prior to use, remove blocking buffer and wash plate 4 times with TBST buffer.

C. Cell Seeding for adherent cells

1. Grow MCF7/HER2 or transfected G8 cells in tissue culture dishes (10 cm, Corning 25020-100) to 80–90% confluence and collect using Trypsin-EDTA (0.25%, GIBCO).
2. Resuspend the cells in fresh medium and transfer to 96-well tissue culture plates (Corning, 25806-96) at 25,000 cells/well (100 μl/well). Incubate the cells in 0.5% calf serum at 37° C. overnight.

D. Seeding for hematopoietic cells

Culture cells in 0.5% calf serum overnight. The next day 5 million cells per well will be seeded in 100 microliters of medium.

II. Assay Procedures.

A. Dilute drug stock (10 mg/ml in DMSO) 1:10 in DMEM medium, then transfer 5 μl to a test well for a final drug dilution of 1:200 and a final DMSO concentration of 1%. Control wells receive DMSO alone. Incubate in 5% $CO_2$ at 37° C. for one hour.

B. Prepare Heregulin or B-cellulin ligand: dilute ligand in media so that upon transfer of 10 μl dilute ligand (1:12 dilution), 25 nM final concentration is attained.

C. Prepare fresh HNTG* sufficient for 100 μl per well; and place on ice.

| HNTG*: | 10 ml |
| HNTG stock | 2.0 ml |
| milli-Q $H_2O$ | 7.3 ml |
| EDTA, 100 mM, pH 7.0 | 0.5 ml |
| $Na_3VO_4$, 0.5M | 0.1 ml |
| $Na_4PO_7$, 0.2M | 0.1 ml |

D. After 60 minute incubation with drug, add prepared heregulin or B-cellulin ligand to cells, 10 μl per well, to a final concentration of 25 nM. Control wells receive DMEM alone. Incubate, at room temperature, for 5 minutes.

E1. For cells in suspension: pellet cells (500 g for 10 minutes at 4 degrees celsius), and aspirate the drug, ligand and media. Remove drug, ligand and medium.

E2. For adherent cells, remove drug, ligand and medium. Wash cells twice with PBS.

F. Transfer HNTG* to cells, 100 μl per well. Place on ice for 5 minutes. Meanwhile, remove blocking buffer from other ELISA plate and wash with TBST as described above.

G. With a pipette tip securely fitted to a micropipettor, scrape cells from plate and homogenize cell material by repeatedly aspirating and dispensing the HNTG* lysis buffer. Transfer lysate to a coated, blocked, and washed ELISA plate. Incubate shaking at room temperature for one hour.

H. Remove lysate and wash 4 times with TEST. Transfer freshly diluted anti-Ptyr antibody to ELISA plate at 100 µl per well. Incubate shaking at room temperature for 30 minutes in the presence of the anti-Ptyr antiserum (1:5000 dilution in TBST).

I. Remove the anti-Ptyr antibody and wash 4 times with TBST. Transfer the freshly diluted TAGO anti-rabbit IgG antibody to the ELISA plate at 100 µl per well. Incubate shaking at room temperature for 30 minutes. anti-rabbit IgG antibody: 1:3000 dilution in TBST J. Remove TAGO detection antibody and wash 4 times with TBST. Transfer freshly prepared ABTS/$H_2O_2$ solution to ELISA plate, 100 µl per well. Incubate at room temperature for 20 minutes. ABTS/$H_2O_2$ solution: 1 µl 30% $H_2O_2$ in 10 ml ABTS stock.

K. Stop reaction by adding 50 µl 5N $H_2SO_4$ (optional), and determine O.D. at 410 nm.

L. The maximal phosphotyrosine signal is determined by subtracting the value of the negative controls from the positive controls. The percent inhibition of phosphotyrosine content for extract-containing wells is then calculated, after subtraction of the negative controls.

EXAMPLE 2.

Sulforhodamine B (SRB) Assay for Adherent Cells

Sulforhodamine B assays for measuring effects of test compounds on cell growth were based on procedures described by Skehan et al. *J. Natl. Cancer Inst.* 82:1107, 1990. Unless otherwise stated the assays were carried out as follows:

Material & Methods
(1) Sulforhodamine B—Sigma Catalog #S-9012 Working solution: 0.4% Sulforhodamine B=4 gram/liter 1% Acetic Acid.
(2) Trichloroacetic Acid (TCA)—Fisher Catalog #A322 Working solution: 10% TCA=100 gram TCA+1 liter $H_2O$.
(3) Acetic Acid, Glacial—Fisher Catalog #A38 Working solution: 1% Acetic Acid=10 ml Acetic Acid+990 ml $H_2O$.
(4) Tris, crystallized free base—Fisher Catalog #BP152 Working solution: 10 mM tris=1.211 gram Trizma base/liter $H_2O$.
(4.5) Heregulin or B-cellulin ligand.

Procedure
(5) Aspirate growth media from 96well plate containing control cells or cell treated with compounds plus or minus ligand, rinse wells 2 or 3 times with PBS and layer 200 µl cold 10% TCA onto each well. Fix cells for 60 minutes at 4° C.
(6) Discard TCA and rinse wells 5 times with distilled $H_2O$. Dry plate upside down on paper towel.
(7) Stain fixed cells for 10 minutes with 100 µl 0.4% SRB per well.
(8) Pour off SRB solution and rinse wells 5 times with 1% acetic acid.
(9) Dry plate upside down on paper towel.
(10) After wells are completely dry, solubilize dye with 100 µl 10 mM Tris base per well for 5–10 minutes on titer plate shaker.
(11) Read optical density at dual wavelength mode 570 nm and 630 nm on Dynatech ELISA plate reader, Model MR 5000.

EXAMPLE 3.

Soft Agar Assay Protocol

The soft agar assay is well known in the art as a method for measuring the effects of substances on cell growth. Unless otherwise stated the soft agar assays were carried out as follows:

Material & Reagents
(1) A Water bath set at 39° C. and another water bath at 3° C.
(2) 2X assay medium is comprised of 2X Dulbecco's Modified Eagle's Medium (DMEM) (Gibco Cat. # CA400-4ANO3) supplemented by the following:
20% Fetal Calf Serum (FCS)
2 mM Sodium Pyruvate
4 mM Glutamine
20 mM HEPES
Non-essential Amino Acids (1:50 from 100x stock)
(3) 1X assay medium made of 1X DMEM supplemented with 10% FCS, 1 mM sodium pyruvate, 2 mM glutamine, 10 mM HEPES, non-essential amino acid (1:100 from 100x stock).
(4) 1.6% SeaPlaque Agarose in autoclave bottle
(5) Sterile 35 mm Corning plates (FMC Bioproducts Cat. #50102)
(6) Sterile 5 ml glass pipettes (individually wrapped)
(7) Sterile 15 ml and 50 ml conical centrifuge tubes
(8) Pipettes and sterile tips
(9) Sterile microcentrifuge tubes
(10) Cells in T75 flasks: MCF7/HER2 or transfected G8 cells.
(11) 0.25% Trypsin solution (Gibco # 25200-015).
(12) Procedure for making the base layer:
(a) Have all the media warmed up in the 37° C. water bath.
(b) To make 1X of assay medium+0.8% agar: make a 1:2 (vol:vol) dilution of melted agar (cooled to 39° C.), with 2X assay medium.
(c) Keep all media with agar warm in the 39° C. water bath when not in use.
(d) Dispense 1 ml of 1 X assay medium+0.8% agar into dishes and gently swirl plate to form a uniform base layer. Bubbles should be avoided.
(e) Refrigerate base layers to solidify (about 20 minutes). Base layers can be stored overnight in the refrigerator.
(13) Procedure for collecting cells:
(a) Take out one flask per cell line from the incubator; aspirate off medium; wash once with PBS and aspirate off; add 3 ml of trypsin solution.
(b) After all cells dissociate from the flask, add 3 ml of 1X assay media to inhibit trypsin activity. Pipette the cells up and down, then transfer the suspension into a 15 ml tube.
(c) Determine the concentration of cells using a coulter counter, and the viability by typan blue exclusion.
(d) Take out the appropriate volume needed to seed 3300 viable cells per plate and dilute it to 1.5 ml with 1X assay medium.

(14) Procedure for making the upper 0.4% agarose layer:
(a) Add test compounds at twice the desired final assay concentration; +1.5 ml of cell suspension in 1X assay medium 10% FCS; +1.5 ml of 1X assay medium+ 0.8% agarose*: Total+3.0 ml 1X media 10% FCS+ 0.4% agarose with 3300 viable cells/ml, with and without test compounds in the presence of heregulin or B-cellulin ligand. *(Made by 1:2 dilution of 2X media with 1.6% agar for the base layer procedure above.)
(b) Plate 1 ml of the Assay Mix onto the 1 ml base layer. The duplicates are plated from the 3 ml volume.
(c) Incubate the dishes for 2–3 weeks in a 100% humidified, 10% $CO_2$ incubator.
(d) Colonies that are 60 microns and larger are scored positive.

Other embodiments are within the following claims.

I claim:

1. A method of identifying an agent that inhibits signal transduction and may be potentially useful in treatment of cancer, comprising:
   a) contacting an agent with a sample comprising a heterodimer having kinase activity, said heterodimer comprising two different components selected from the group consisting of HER2, HER3, and HER4, to render a HER2/HER3 heterodimer, a HER2/HER4 heterodimer, or a HER3/HER4 heterodimer; and
   b) determining whether said agent inhibits said kinase activity, wherein inhibition of kinase activity is indicative of an agent that inhibits signal transduction.

2. The method of claim 1, wherein said heterodimer is present in a cell.

3. The method of claim 2, wherein said cell contains a recombinant nucleic acid encoding at least one component selected from the group consisting of said HER2, HER3, and HER4.

4. The method of claim 2, wherein said cell is selected from the group consisting of a human breast adenocarcinoma cell, a mouse fibroblast cell, and a hematopoietic cell.

5. The method of claim 1, wherein said inhibition of signal transduction is mediated by inhibition of the kinase activity of said heterodimer.

6. The method of claim 1, wherein said agent has a molecular weight of less than 3000.

7. The method of claim 1, wherein said agent is selected from the group consisting of quinazolines, tyrphostins and quinoxalines.

8. The method of claim 1, wherein said agent inhibits the stimulation of signal transduction by a ligand selected from the group consisting of gp30, neu differentiation factor, heregulin, and Beta-cellulin which is added to said sample, wherein said ligand is able to mediate the kinase activity of said HER2/HER3 heterodimer, said HER3/HER4 heterodimer, or said HER2/HER4 heterodimer.

9. The method of claim 8, wherein said ligand is beta-cellulin or heregulin.

10. The method of claim 8, wherein said agent is contacted with said sample prior to addition of said ligand.

11. The method of claim 1, wherein said determining step comprises measuring the level of phosphorylation of at least one of said HER2, said HER3 or said HER4.

12. A method of screening for an agent that specifically inhibits the kinase activity of a HER2 or HER4 receptor tyrosine kinase and may be potentially useful in treatment of cancer, comprising:
   a) contacting an agent with a sample comprising a HER2/HER3, HER2/HER4, or HER3/HER4 heterodimer having kinase activity, said heterodimer comprising a catalytically active receptor tyrosine kinase selected from the group consisting of HER2 and HER4 conjugated to a catalytically inactive receptor tyrosine kinase selected from the group consisting of HER 2, HER3 and HER4; and
   b) determining whether said agent inhibits the kinase activity of said heterodimer, wherein inhibition of kinase activity is indicative of an agent that specifically inhibits the kinase activity of a HER2 or HER4 receptor tyrosine kinase.

13. The method of claim 12, wherein said heterodimer is a HER2/HER4 heterodimer and said catalytically inactive receptor tyrosine kinase is HER2.

14. The method of claim 12, wherein said heterodimer is a HER2/HER4 heterodimer and said catalytically inactive receptor tyrosine kinase is HER4.

15. A method of screening for an agent that specifically inhibits the kinase activity of a HER2 component or a HER4 component of a HER2/HER4 heterodimer and may be potentially useful in treatment of cancer, comprising
   a) contacting an agent with a sample comprising a HER2/HER4 heterodimer comprising a HER2 component and a HER4 component, wherein one of said HER2 and HER4 components lacks kinase activity; and
   b) determining whether said agent inhibits the kinase activity of said heterodimer, wherein inhibition of kinase activity is indicative of an agent that specifically inhibits the kinase activity of a HER2 or HER4 component.

16. A method of screening for an agent that specifically inhibits the kinase activity of a HER2 or HER4 receptor tyrosine kinase and may be potentially useful in treatment of cancer, comprising:
   a) contacting an agent with a cell comprising a heterodimer to form a first sample, wherein said heterodimer comprises i) a first receptor tyrosine kinase component that possesses kinase activity, said first receptor tyrosine kinase component selected from the group consisting of HER2 and HER4 and associated with ii) a second receptor tyrosine kinase component that lacks kinase activity, said second tyrosine component selected from the group consisting of HER2, HER3 or HER4;
   b) determining the level of signal transduction by measuring kinase activity or cell growth in said cell in said first sample;
   c) adding a ligand selected from the group consisting of gp30, neu differentiation factor, heregulin, and Beta-cellulin that stimulates the kinase activity of said heterodimer to said first sample, thereby forming a second sample;
   e) determining the level of signal transduction by measuring kinase activity or cell growth in said second sample; and
   f) comparing the levels of signal transduction in said first sample and said second sample, thereby determining whether said agent inhibits the kinase activity of a HER2 or HER4 receptor tyrosine kinase.

17. The method of claim 16, wherein said steps c) and e) comprise measuring HER2 kinase activity.

18. The method of claim 16, wherein said steps c) and e) comprise measuring phosphorylation of HER2 or a HER2 substrate.

* * * * *